US008556819B2

(12) United States Patent
Röher et al.

(10) Patent No.: US 8,556,819 B2
(45) Date of Patent: Oct. 15, 2013

(54) TREATMENT DEVICE WITH MEMORY-SUPPORTED CONTROL MEANS

(75) Inventors: Otfried Röher, Dresden (DE); Steffen Korth, Elleben (DE)

(73) Assignee: B. Braun Avitum AG, Melsungen (DE)

( * ) Notice: Subject to any disclaimer, the term of this patent is extended or adjusted under 35 U.S.C. 154(b) by 874 days.

(21) Appl. No.: 12/441,176

(22) PCT Filed: Sep. 11, 2007

(86) PCT No.: PCT/EP2007/059524
§ 371 (c)(1), (2), (4) Date: Aug. 13, 2009

(87) PCT Pub. No.: WO2008/031821
PCT Pub. Date: Mar. 20, 2008

(65) Prior Publication Data

US 2010/0016776 A1 Jan. 21, 2010

(30) Foreign Application Priority Data

Sep. 15, 2006 (EP) .................................... 06120761

(51) Int. Cl.
*A61B 5/02* (2006.01)
*B01D 11/00* (2006.01)
*B01D 61/00* (2006.01)

(52) U.S. Cl.
USPC ............................ 600/485; 210/645; 210/646

(58) Field of Classification Search
USPC ............... 604/4.01, 5.01, 6.01; 210/645, 646; 600/485
See application file for complete search history.

(56) References Cited

U.S. PATENT DOCUMENTS 4,710,164 A 12/1987 Levin et al.
6,423,022 B1 * 7/2002 Roeher et al. ................ 604/5.01
2002/0107449 A1 8/2002 Roeher
2003/0209475 A1 11/2003 Connell et al.

FOREIGN PATENT DOCUMENTS

DE 28 25 134 A1 12/1978
EP 0 956 872 A2 11/1999
EP 1 226 838 A2 7/2002

OTHER PUBLICATIONS

International Search Report, dated Dec. 17, 2007.

* cited by examiner

*Primary Examiner* — Melanie Hand
(74) *Attorney, Agent, or Firm* — RatnerPrestia

(57) ABSTRACT

The therapy device stores the time profiles of the blood pressure and of other influencing variables during preceding therapy procedures. The time profile of the blood pressure and of other influencing variables during the actual therapy is also recorded. An analytical comparison is then made between the time profiles of the blood pressure and of other influencing variables during the actual measurement procedure and those during preceding therapy procedures. Depending on the comparison, a prospective blood pressure control is carried out in order to prevent drops in blood pressure in a subsequent time period.

8 Claims, 3 Drawing Sheets

19 18 10 11 13 12 16 24 17 20 14 36 15 25 UFR 23 BP

TREATMENT DEVICE WITH MEMORY-SUPPORTED CONTROL MEANS

This is a U.S. National Phase application of application number PCT/EP2007/059524, filed Sep. 11, 2007 (which is incorporated herein by reference in its entirety), which claims priority benefit of EP 06 120 761.9 filed Sep. 15, 2006.

FIELD OF THE INVENTION

The invention relates to a therapy device comprising a blood-pressure measuring device and a memory-supported control means for controlling the points of time of blood-pressure measurements and for controlling the blood pressure of the patient during a therapy procedure, and particularly a therapy device for extracorporeal purification of blood.

BACKGROUND OF THE INVENTION

In various therapies, e.g. in hemodialysis, it is required that the blood pressure of the patient is continuously monitored. For this purpose, use is made of devices for indirect (non-invasive) blood-pressure measurement with the aid of a cuff to be laid around the patient's arm, which cuff will be inflated and then will be slowly deflated while a pressure measurement process will be performed at the same time. For achieving a quasi-continuous blood-pressure control, the control means has to perform control processes in intervals of a few minutes. The number of blood-pressure measurements required for such a control process during a treatment procedure covering several hours can be considerably reduced if, at predetermined points of time, blood-pressure measurements are substituted by blood-pressure values which were obtained in earlier treatment procedures performed on the same patient. U.S. Pat. No. 6,578,241 B2 and EP 1 226 838 A2 describe corresponding therapy devices with interval-based blood-pressure measurement and a reduced number of measurement processes. Herein, on the basis of an identical length of all intervals, e.g. five minutes per interval, the control means safeguards that the blood-pressure development and the blood-pressure trends will be evaluated in each interval in accordance with uniform rules, as is described in EP 0 956 872 A2.

SUMMARY OF THE INVENTION

One embodiment of the present invention involves the use of a therapy device described in EP 1 226 838 A2. This therapy device performs blood-pressure measurements at intervals and, in dependence thereon, controls the ultrafiltration rate UFR to the effect that no inadmissible drops in blood pressure will occur. At those times when no measurement of the blood pressure is performed, the values of a guide curve obtained in preceding therapy procedures will be taken as actual values of the blood pressure, and at the times of blood-pressure measurement, the real actual values of the blood-pressure development will be evaluated.

In clinical practice, since possible morbid events during hemodialysis, such as hypotonia, attacks of dizziness, vomiting et al., have to be attributed to multifactorial causes, use is sometimes made of monitors for further variables (e.g. ECG, relative blood volume, hemotacrit, blood oxygen content) so that complications can be detected. Depending on the measurement results, this approach may entail a requirement for additional blood-pressure measurements at random points of time. Clinical experience with dialysis patients has evidenced that, in dependence on the patient's condition, blood-pressure measurements may also have to be requested directly by the medical personnel. A corresponding therapy device with temporally flexible blood-pressure control is described in the (non-prepublished) European Patent Application No. 06 112 431.9.

In the above mentioned therapy devices, blood-pressure control is basically performed only on the basis of values and temporal developments of the preceding therapy procedures up to the actual treatment time. The values and temporal developments of the preceding therapy procedures for the time periods after the actual treatment time up to the end of the treatment, which will also be stored in the therapy devices, will not be considered in the blood-pressure control.

However, as shown by clinical experience with dialysis patients, these time periods of preceding therapy procedures can be useful for deriving from them substantial information about the prospective blood-pressure development after the respective treatment time of the actual treatment. It appears promising that such information —particularly for the same patient with comparable treatment parameters such as, e.g., total ultrafiltration volume, maximal ultrafiltration rate, dialysate conductivity, length of treatment—may lead to important conclusions which in clinical practice can be routinely used for a prospective blood-pressure control. In connection with analytic comparisons, performed with the aid of statistic similarity criteria, between the temporal developments of the blood pressure and between other relevant influential parameters during the actual treatment and during preceding treatment procedures, it is possible to achieve favorable preconditions for a prediction of impending drops in blood pressure.

Thus, it is an object of the invention to configure a therapy device in such a manner that, with the aid of a memory-supported control means, the future development of the blood pressure can be predicted and a prospective control of the blood pressure can be performed.

According to the invention, the above object is achieved by the features defined herein. The memory-supported control means is configured to perform the following further functions after a blood-pressure measurement:

analyzing the developments of the blood pressure of said selected preceding therapy procedures in time periods following the actual point of time of the actual therapy procedure for detection of drops in blood pressure, and selecting at least one of the preceding therapy procedures with a drop in blood pressure in the subsequent time periods; and prospective blood-pressure control for prevention of drops in blood pressure, wherein the temporal development of said at least one selected therapy procedure is used as a guide value of said prospective blood-pressure control in the time periods following the actual point of time.

According to the invention, it is provided that, in time periods following the actual point of time of the actual therapy procedure, the developments of the blood pressure of preceding therapy procedures are checked for drops in blood pressure. In this manner, those preceding therapy procedures in which at least one drop in blood pressure occurred in a time period following the actual point of time of the actual therapy procedure, will be selected, and, for the control process, there will be used only the developments of these selected therapy procedures. The inclusion of the temporal developments of the blood pressure (and, if desired, of further relevant influential variables) from preceding therapy procedures allows for a prediction of future drops in blood pressure and for a prospective blood-pressure control on the basis of patient-specific experiences. Under comparable therapy conditions with respect to the treatment characteristics predefined by the medical personnel, such as e.g. total ultrafiltration volume, length of therapy, maximal ultrafiltration rate, dialysate conductivity and limiting values of the blood-pressure control range, there was accomplished a prediction of abnormities, such as e.g. drops in blood pressure within the subsequent time period of e.g. 30 minutes, with a hit rate of above 85%.

By the prospective blood-pressure control aspect, it is meant that the blood-pressure control following the actual point of time is a “prospective blood-pressure control” which is oriented on a selected temporal development as a guide value.

Since the criterion “drop in blood pressure” is considered already during the selection, the control of the blood pressure is performed in such a manner that the future drops in blood pressure will be avoided with high likelihood.

Particularly for patients at risk of hypotony, the invention considerably contributes to a prevention of drops in blood pressure and to a quality improvement of the dialysis treatment.

Preferably, the memory-supported control means, which inter alia is operative to control the interval-based blood-pressure measurements, will perform the following steps:

- storage of the blood-pressure measurement values for a fixed number of therapy procedures inclusive of therapy procedures taken over, in the form of guide curves, from preceding therapy procedures at fixed points of time, and of the guide values of the memory-supported control process (e.g. ultrafiltration rate, dialysate conductivity
- storage of further treatment parameters (e.g. total ultrafiltration volume, maximum ultrafiltration rate, length of therapy, limiting values of the blood-pressure control range) of the therapy procedures stored according to d),
- analysis and classification of the blood-pressure values mentioned under d) for different time periods of the preceding therapy procedures, in correspondence to their similarity to the development of the blood pressure of the actual therapy procedure,
- determination of measures for prospective blood-pressure control for the used guide values on the basis of those preceding therapy procedures which have the highest similarity to the actual development of the blood pressure,
- adaptation of the control characteristics in correspondence to the measures determined in said determination step in dependence on the actual development of the blood pressure and on the point of time during the actual therapy procedure.

By the memory-supported control means, the following criteria of blood-pressure values will be included in the prospective blood-pressure control:

- blood-pressure values detected through interval-based measurements according to the time regime implemented in the control means, as is described in European Patent Application EP 0 956 872 B1, and
- blood-pressure values which are substituted in the form of guide curves from preceding therapy procedures for reduction of the number of blood-pressure measurements, as is described in European Patent Application EP 1 226 838 A2, and
- blood-pressure values which are automatically requested at other times by connected measurement and analysis devices for other physiological values (e.g. ECG, relative blood volume, hemocrit, blood-oxygen content), as is described in European Patent Application EP 06 112 431.9, and
- blood-pressure values which are requested through manual input by the medical personnel at other times, as is described in European Patent Application EP 06 112 431.9.

According to one embodiment of the invention, it is provided that, after each blood-pressure measurement, the memory-supported control means will analyze all stored developments of the therapy of the respective patient with regard to their similarity to the actual development of the blood pressure. In order to always guarantee an up-to-date data pool, storage of maximally 100 treatments per patient is provided (n=100). In case of the usual treatment rhythm of three dialyses per week, the stored data pool represents the treatments of up to 33 weeks and thus about eight months at maximum. Upon storage of the 101st treatment, the 1st treatment will be automatically deleted. Thereby, a continuous actualization of the data pool is safeguarded.

According to another embodiment of the invention, it is further provided that, after each blood-pressure measurement, there will be analyzed, for use in prospective blood-pressure control, a predetermined number—e.g. three to five—of preceding treatments having the respective closest similarities to the actual development of the blood pressure. Thereby, it is safeguarded that, in the interest of a highest possible predictability of future drops in blood pressure, consideration will be given only to treatments whose similarity is markedly different from the majority of the stored treatments. The similarity analyses preferably cover the time periods from the start of the treatment up to the actual point of time or only up to 15 to 20 minutes prior to the actual point of time, or a combination of both variants.

According to another embodiment of the invention, it is further provided that the prospective blood-pressure control will be activated as soon as the majority of the analyzed three to five preceding therapy procedures in the subsequent time period of about 30 minutes have blood-pressure values within the active blood-pressure control range. The memory-supported control means will then react with a reduction of the ultrafiltration rate and/or an increase of the dialysate conductivity.

The invention is particularly suited for dialysis devices and other devices for extra-corporeal purification of blood but also e.g. for infusion therapy.

An embodiment of the invention will be explained in greater detail hereunder with reference to the drawings.

DETAILED DESCRIPTION OF THE INVENTION

Figure 1:
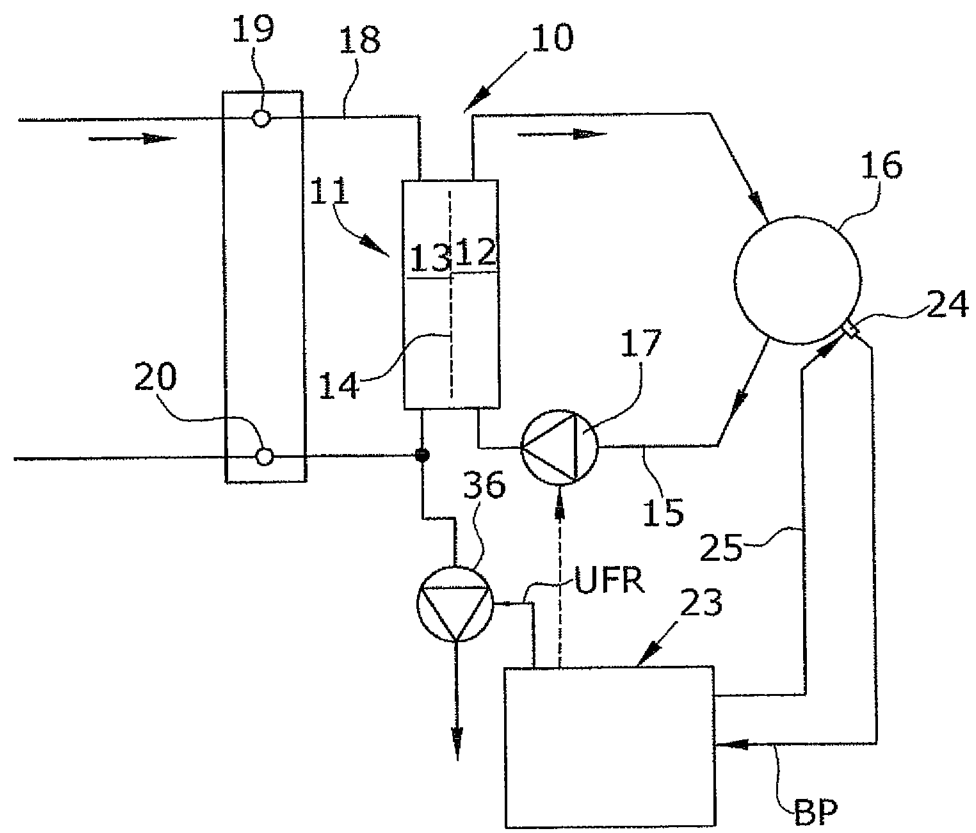
FIG. 1 is a schematic view of a dialysis device.

The dialysis device illustrated in FIG. 1 is of a basic layout corresponding to that according to EP 0 956 872 B1 or EP 1 226 838 A2. The dialysis device includes an ultrafiltration means 11 with a primary chamber 12 and a secondary chamber 13, said chambers being separated from each other by a membrane 14. Primary chamber 12 is a component of a blood circuit 15 wherein blood which has been taken from the patient via the arterial system, will be purified in ultrafiltration means 11 and then be returned to the patient 16 via the venous system. In the blood circuit 15, a pump 17 is arranged.

The pump is designed as a volumetric pump, i.e. the delivery volume of the pump corresponds to the driving speed of the pump, and the pump further is of the controllable type.

The secondary chamber 13 of ultrafiltration means 11 is arranged in a dialyzing liquid path 18 into which dialyzing liquid is conveyed by pumping. The dialyzing liquid is fed from a supply container (not shown) and will then, in the ultrafiltration means 11, take up additional substances from the blood and thereafter will be pumped to a discharge duct (not illustrated). In the dialyzing liquid path, at positions upstream and downstream of the secondary chamber 13, respectively one flow chamber 19 and resp. 20 is arranged for controlling the flow rate at the respective position. Flow chamber 19 and flow chamber 20 have the same conveying rate. Via a volume-controlled ultrafiltration pump 36, the desired ultrafiltration volume UFV is withdrawn at a fixed ultrafiltration rate UFR. The time integral over the ultrafiltration rate UFR forms the ultrafiltration volume UFV, i.e. that liquid volume which has passed the membrane 14 since the start of the treatment. The control of the ultrafiltration rate is carried out by a control means 23 which is operative to deliver control signals for the delivery rate of pump 36. The delivery rate of the pump is suitably set to the effect that a desired ultrafiltration rate is achieved.

Said control means 23 further receives the blood-pressure signal BP of a blood-pressure measuring apparatus 24 attached to the arm of the patient. The blood-pressure measuring apparatus comprises an inflatable cuff laid around the patient's arm, and performs non-invasive blood pressure measurements. The points of time of the blood pressure measurements are determined internally by the control means 23 via lines 25, and internally by connected monitors and/or the medical personnel. Apart from the blood-pressure value, also blood-pressure trend values can be fed to the control means 23, as described in EP 0 956 872 B1. Control means 23 operative to control the ultrafiltration rate UFR in dependence on the received input values.

Figure 2:
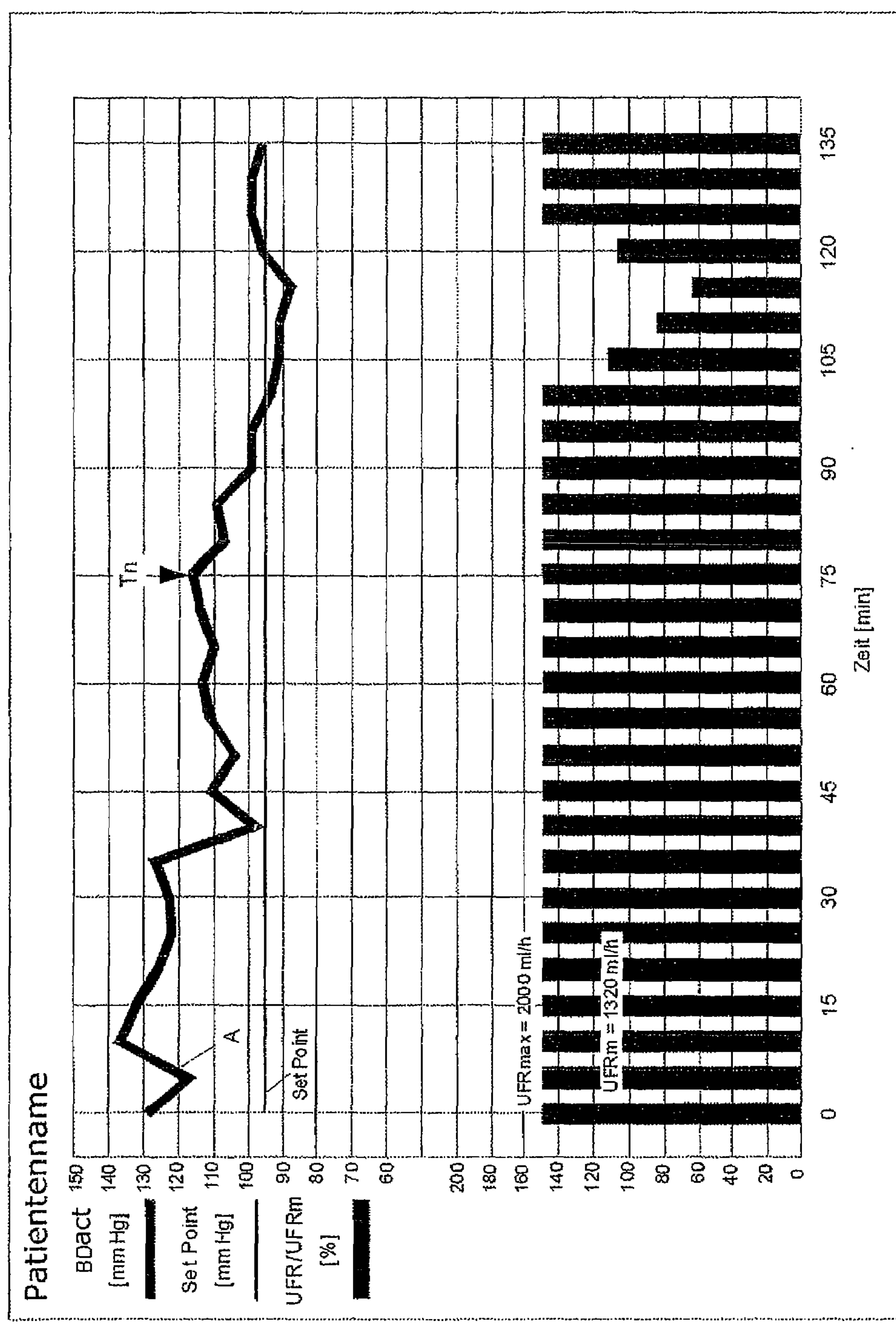
FIG. 2 is a time diagram of a dialysis treatment (excerpt) without prospective blood pressure control.

In FIG. 2, the blood-pressure control, as heretofore performed by the control means 23 without prospective blood-pressure control, is illustrated by the example of a dialysis treatment. At the observed point of time Tn=75 minutes, the blood-pressure measurement performed according to this example will result in a blood pressure distinctly above the upper limiting value of the active control range of the control means. In FIG. 2, this upper limiting value is a plotted as a set point. Thus, the control means will not perform a reduction of the ultrafiltration rate on the basis of the development of the blood-pressure curve A, thus maintaining the maximum ultrafiltration rate UFRmax=2000 ml/h preselected by the medical personnel. UFRmax in the actual example is about 150% of the average ultrafiltration rate UFRm=1320 ml/h resulting from the predetermined dialysis target (total ultrafiltration volume and length of treatment). The drop in blood pressure below the set point occurring at a later time at 100 minutes is not detected by the heretofore used control means without prospective blood-pressure control because, in this control means, stored developments of the blood pressure from preceding treatments are considered only up to the respective point of time of the treatment (in FIG. 2: Tn=75 min). Thus, in this example, it is only at the time when the blood pressure drops below the set point, i.e. after 100 min, that the control means will start to reduce the ultrafiltration rate.

Figure 3:
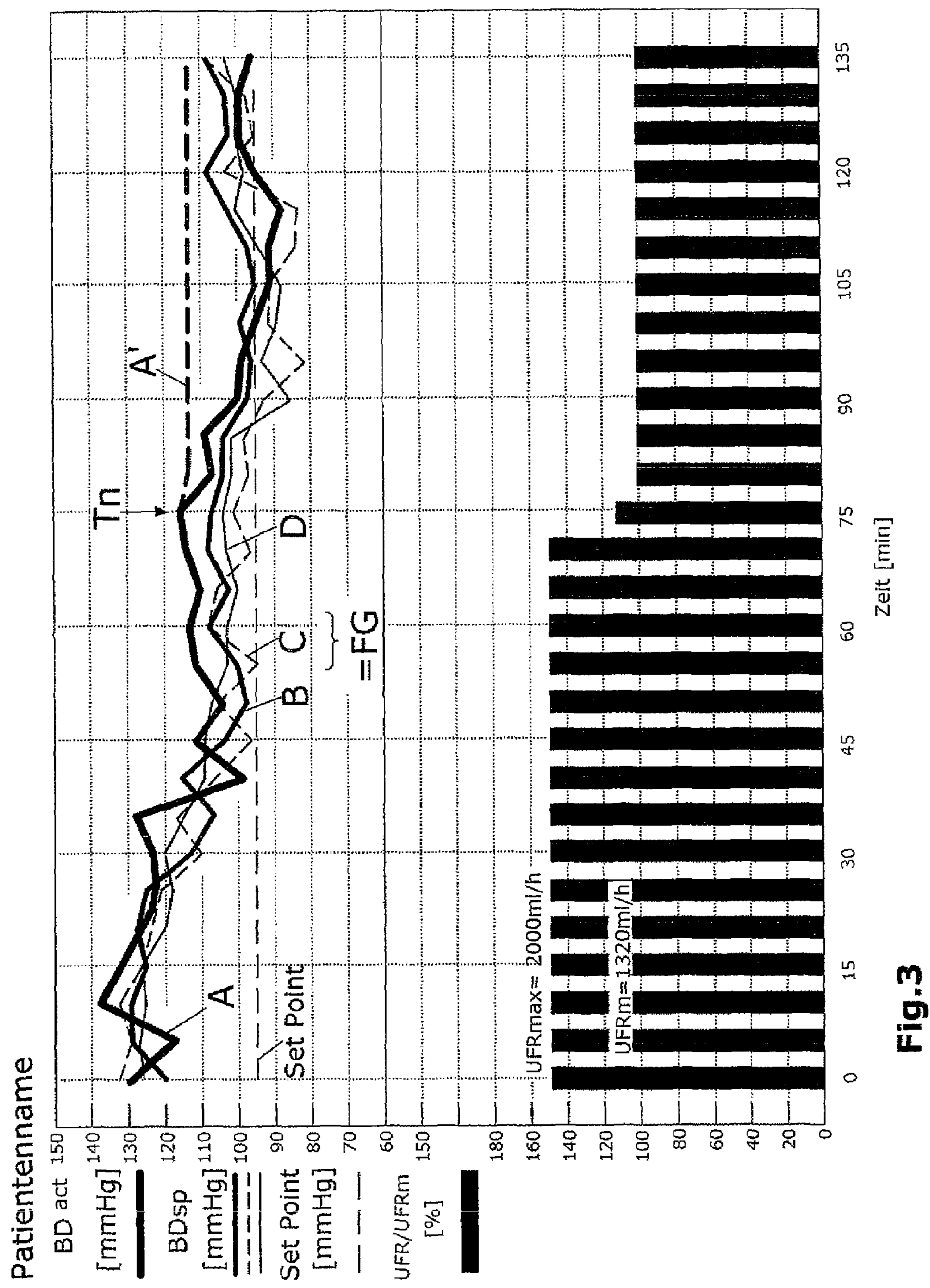
FIG. 3 is a time diagram of a dialysis treatment (excerpt) with prospective blood-pressure control.

In FIG. 3, the advantages of a control means of the invention, designed for prospective blood-pressure control, are exemplified for the same blood-pressure development A up to the observed time of the treatment Tn=75 min as in FIG. 2. Additionally plotted in FIG. 3 are the stored blood-pressure values BDsp of the three blood-pressure curves B, C and D from preceding treatments, which values—according to the similarity criteria, implemented in the control means, for the actual treatment period from 0 min up to 75 min—have the highest similarity to the actual blood-pressure development BDact. The similarity criteria herein result from statistical analyses of the blood-pressure developments (e.g. average values, deviations from the standard, t-tests, sample recognition).

The memory-supported control means with prospective blood-pressure control will detect already now, at the observed point of time of the treatment Tn=75 min, that two of the three selected blood pressure curves from preceding treatments in the selected prediction time period Tn+30 min, i.e. in the subsequent treatment period from 75 min to 105 min, include drops in blood pressure below the set point, namely the curves C and D.

Since physiological reaction times of several minutes have to be taken into account between a change of the ultrafiltration rate and the associated change of the blood pressure, the prospective blood-pressure control will for this reason be performed on the basis of an analysis of the stored blood-pressure developments BDsp of the selected preceding therapy procedures in the time period Tn+15 min up to Tn+30 min. For the prospective blood-pressure control, the points of time as well as the depth of the drops in blood pressure are of essence herein. For the curves C and D in the example illustrated in FIG. 3, the points of time of the drops in blood pressure are below the set point at 90 min. In the time period from 90 min to 105 min, however, the extent of the drop in blood pressure for curve C is considerably larger than for curve D. Therefore, in this example, the control means selects the blood-pressure development of curve C from Tn+15 min=90 min and uses this development as a guide value FG of the prospective blood-pressure control for the treatment period from Tn=75 min up to the next blood-pressure control.

For this reason, the control means initiates already now, at Tn=75 min, a prospective reduction of the ultrafiltration rate with the objective that, in this manner, a drop in blood pressure below the set point as in curve A will be avoided or at least be minimized in the actual treatment. In FIG. 3, this target function is schematically outlined by the hypothetical blood-pressure development A' which is to be expected. Substantial influential values of the actual treatment and of the selected blood-pressure developments B, C and D such as e.g. total ultrafiltration volume, length of therapy, maximal ultrafiltration rate, upper and lower limiting values of the blood-pressure control range, will be considered in the determining of the respective reduction of the ultrafiltration rate.

The memory-supported control means with prospective blood-pressure control will repeat the operational steps illustrated in FIG. 3 after each blood-pressure measurement. In the implemented time regime, time periods of 15 min to 30 min are preset for this repetition in dependence on the currently running treatment time and the already withdrawn ultrafiltration volume. Thus, by each subsequent blood-pressure measurement, the actual development A' during the current treatment can be improved in the sense of a step-wise optimization of the treatment.

The invention claimed is:

1. A therapy device for extracorporeal blood treatment, comprising:

a blood-pressure measuring device and a memory-supported controller that controls blood pressure of a patient using settable treatment parameters, wherein said memory-supported controller is configured to perform the following functions during a current therapy procedure:

a) detecting and storing a temporal development of the blood pressure during the current therapy procedure;

b) analytically comparing the temporal development of the blood pressure up to a current point of time during the current therapy procedure with temporal developments of the blood pressure of preceding therapy procedures up to a respective point of time corresponding to the current point of time of the current therapy procedure;

c) selecting the temporal developments of the blood pressure of the preceding therapy procedures that are most similar up to the respective point of time to the temporal development of the blood pressure of the current therapy procedure up to the current point of time of the current therapy procedure;

d) analyzing the selected temporal developments of the blood pressure of the preceding therapy procedures to detect in the selected temporal developments of the blood pressure of the preceding therapy procedures a decrease in the blood pressure beyond the respective point of time;

e) choosing at least one of the selected temporal developments of the blood pressure of the preceding therapy procedures having the decrease in the blood pressure beyond the respective point of time; and f) preventing a decrease in the blood pressure of the current therapy procedure, wherein the temporal development of the at least one the selected temporal developments of the blood pressure of the preceding therapy procedures beyond the respective point of time used as a guide value to prospectively control the blood-pressure in time periods beyond the current point of time of the current therapy procedure.

2. The therapy device according to claim 1, wherein said controller is configured to repeatedly perform functions (b)-(e).

3. The therapy device according to claim 1, wherein said controller is operative to decide from which preceding therapy procedures the guide value is to be taken over for the time period beyond the current point of time of the current therapy procedure.

4. The therapy device according to claim 1, wherein temporal developments of blood-pressure-relevant influencing variables and the settable treatment parameters are detected and stored; and at least one of said temporal developments of blood-pressure-relevant influencing variables from the selected preceding therapy procedures is used as an additional guide value in time periods following the current point of time of the current therapy procedure.

5. The therapy device according to claim 1, wherein the detection of a similarity of preceding therapy procedures to the current therapy procedure is based on the time periods from the start of the therapy procedure up to the current point of time of the current therapy procedure, and/or less than 20 minutes prior to the current point of time of the current therapy procedure.

6. The therapy device according to claim 1, wherein, by the memory-supported controller, all or some of the following categories of blood-pressure values or blood-pressure-influencing variables are used to prospectively control the blood pressure:

blood-pressure values which are detected by interval-based measurements according to the time regime implemented in the controller, blood-pressure values which are substituted in the form of guide curves from preceding therapy procedures for thus reducing the number of blood-pressure measurements, blood-pressure values or blood-pressure-influencing variables which are automatically requested by measurement and analysis devices for other physiological values, and blood-pressure values which are requested through manual input by the medical personnel.

7. The therapy device according to claim 4, wherein the blood-pressure-relevant influencing variables include at least one of ultrafiltration rate, dialysate conductivity, or infusion quantity.

8. The therapy device according to claim 4, wherein the settable treatment parameters include at least one of total ultrafiltration volume, maximum ultrafiltration rate, or length of treatment.

* * * * *

UNITED STATES PATENT AND TRADEMARK OFFICE

CERTIFICATE OF CORRECTION

PATENT NO. : 8,556,819 B2
APPLICATION NO. : 12/441176
DATED : October 15, 2013
INVENTOR(S) : Röher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1108 days.

Signed and Sealed this
Fifteenth Day of September, 2015

Michelle K. Lee
*Director of the United States Patent and Trademark Office*